United States Patent

Diehr et al.

[11] Patent Number: 5,756,752
[45] Date of Patent: May 26, 1998

[54] PROCESS FOR PREPARING SUBSTITUTED OXADIAZOLONES

[75] Inventors: Hans Joachim Diehr; Reinhard Lantzsch, both of Wuppertal, German Dem. Rep.; Jacqueline M. Applegate, Parkville, Mo.; Klaus Jelich, Overland Park, Kans.

[73] Assignees: Bayer Corporation, Pittsburgh, Pa.; Bayer Aktiengesellschaft, Leverkusen, Germany

[21] Appl. No.: 842,585

[22] Filed: Apr. 15, 1997

[51] Int. Cl.$^6$ ............... C07D 271/07; C07C 243/20; C07B 41/04
[52] U.S. Cl. ............... 548/132; 562/606; 562/847; 564/310
[58] Field of Search ............... 548/132

[56] References Cited

U.S. PATENT DOCUMENTS

| | | | |
|---|---|---|---|
| 3,951,996 | 4/1976 | Stanley et al. | 260/295 |
| 4,952,701 | 8/1990 | Müller et al. | 548/263.8 |

FOREIGN PATENT DOCUMENTS

| | | |
|---|---|---|
| 2135449 | 5/1995 | Canada. |
| 301946 | 2/1989 | European Pat. Off. |

OTHER PUBLICATIONS

Bull Chem. Soc. Japan 44 (Month unavailable) (1971), 870.
Chem Ber. 98 (Month unavailable) (1965), 540–545.
Helv. Chim. Acta 55 (Month unavailable) (1972), 1174–1178.
J. Org. Chem. 26, (Jun. 1961), 1843–1846.
J. Org. Chem. 30, (Month unavailable) (1965), 2486–2488.

*Primary Examiner*—Johann Richter
*Assistant Examiner*—Jane C. Oswecki
*Attorney, Agent, or Firm*—Joseph C. Gil

[57] ABSTRACT

Substituted oxadiazolones of the formula (I)

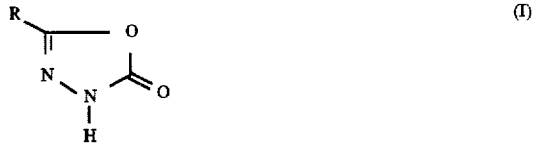

in which

R represents optionally substituted alkyl, are obtained in good yields and high purity on reacting in a first step carboxylic acids of the general formula (II)

R—COOH     (II)

with hydrazine hydrate in the presence of a catalyst and an inert diluent at temperatures between 0° C. and 150° C. with elimination of water and removal of said catalyst and reacting the resulting carboxylic hydrazides of the general formula (III)

R—CO—NH—NH$_2$     (III)

in a second step with phosgene (COCl$_2$) at temperatures between 20° C. and 120° C.

9 Claims, No Drawings

PROCESS FOR PREPARING SUBSTITUTED OXADIAZOLONES

BACKGROUND OF THE INVENTION

The present invention relates to a novel process for preparing substituted oxadiazolones known as intermediates for preparing herbicidally active compounds. The present invention also relates to the preparation of acylated hydrazines used to prepare the oxadiazolones.

It is known that certain substituted oxadiazolones, such as, for example, 5-methyl-1,3,4-oxadiazol-2(3H)-one, are obtained when acylated hydrazines, such as, for example, acethydrazide, are reacted with phosgene (cf. Bull. Chem. Soc. Japan 44 (1971), 870; Chem. Ber. 98 (1965), 540–545; Helv. Chim. Acta 55 (1972), 1174–1178; J. Org. Chem. 26 (1961), 1843–1846; and European patents 301,946 and 321,833).

The acylated hydrazines required as starting materials are generally prepared in a prior reaction step from the corresponding carboxylic acids and hydrazine (hydrate) in the presence of catalysts and in the presence of hydroxy functional solvents such as 2-methyl-1-butanol or n-butanol or mixtures of such hydroxy functional solvents and toluene e or benzene (see, e.g., J. Org. Chem. 30 (1965), 2486–2488; British patent 1,396,615; European patent 653,419).

However, the two reactions are generally carried out in different solvents. This is unfavorable for industrial purposes, since the solvents used can not be readily recycled or recovered in pure form. According to the prior art, the acylated hydrazines have to be isolated and dried by a complicated procedure prior to the subsequent phosgenation. It is therefore an object of the present invention to provide a process for preparing substituted oxadiazolones which is better suited to industrial purposes.

DESCRIPTION OF THE INVENTION

The present invention is directed to two broad embodiments. In the first embodiment, a carboxylic acid is reacted with hydrazine hydrate in the presence of a catalyst and in the presence of an inert diluent and in the absence of an hydroxy functional solvent at temperatures between 0° C. and 150° C. with elimination of water and subsequent removal of the catalyst. In the second (and preferred) embodiment, the acylated hydrazine so-produced is reacted with phosgene at temperatures between 20° C. and 120° C.

More particularly, the present invention is directed to a process for producing substituted oxadiazolones of the general formula (I)

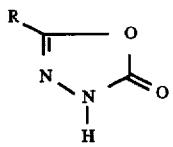

in good yields and in high purity comprising:

(a) reacting carboxylic acids of the general formula (II)

R—COOH (II)

with hydrazine hydrate in the presence of a catalyst and in the presence of an inert diluent and in the absence of an hydroxy functional solvent at temperatures between 0° C. and 150° C. with elimination of water and removal of said catalyst, and (b) reacting the resulting carboxylic hydrazides of the general formula (III)

R—CO—NH—NH$_2$ (III)

in a second step in the same reaction medium with phosgene (COCl$_2$) at temperatures between 20° C. and 120° C.

In all of the above identified formula, R represents an alkyl group which may be substituted.

It is very surprising that the reaction of carboxylic acids with hydrazine hydrate can be carried out without any problems in inert solvents without using alcohols or alcohol-benzene or alcohol-toluene mixtures and that the following reaction with phosgene proceeds with good results even without the isolation of the intermediate isolated hydrazines and without changing the solvent.

The process according to the invention therefore represents a useful advance in the art. The process according to the invention preferably relates to the preparation of compounds of the formula (I) in which R represents a straight-chain or branched alkyl having 1 to 6 carbon atoms, which may be substituted with halogen-atoms or C$_1$-C$_4$-alkoxy groups.

The process according to the invention more preferably relates to the preparation of compounds of the formula (I) in which R represents an alkyl group selected from the group consisting of methyl, ethyl, n-propyl, i-propyl, n-butyl, i-butyl, s-butyl and t-butyl, each of which may be substituted with a moiety selected from the group consisting of fluorine, chlorine, methoxy and ethoxy If, for example, acetic acid and hydrazine hydrate are employed as starting materials, the process according to the invention can be represented by the following scheme:

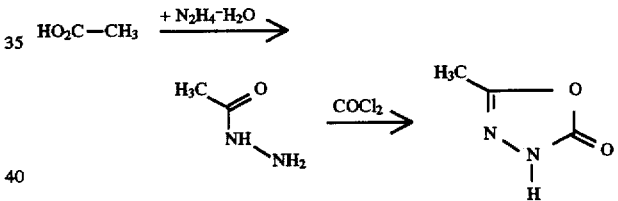

The carboxylic acids to be used as starting materials in the process according to the invention are defined in a general way by formula (II). In formula (II), R has preferably and more preferably those meanings already listed above in connection with the description of the compounds of the formula (I).

The starting materials of the formula (II) are known organic chemicals.

The process according to the invention is carried out in the presence of a catalyst. Suitable catalysts are, in particular, substances accelerating condensation reactions—i.e. reactions proceeding with the elimination of water—of carboxylic acids with alcohols, amines, hydrazines, and the like. These include (optionally activated) aluminum oxide, titanium dioxide, zirconium oxide, aluminum alkoxides, titanium alkoxides or zirconium alkoxides, or aluminum halide alkoxides, titanium halide alkoxides or zirconium halide alkoxides, such as, for example, aluminum tri-i-propoxide, titanium tetramethoxide, titanium tetraethoxide, titanium tetra-n-propoxide, titanium tetra-i-propoxide, titanium tetra-n-butoxide, titanium tetra-i-butoxide or titanium tetra-s-butoxide.

Particularly preferred catalysts are aluminum oxide, titanium dioxide, titanium tetra-n-propoxide and titanium tetra-i-propoxide. Surprisingly, the metal oxides mentioned are active even when they are present as hydrates, i.e. contain water. Therefore, it is optionally possible to recover and recycle the catalyst.

The process according to the invention is carried out in the presence of an inert diluent. As used herein, the phrase "inert diluent" is defined as those organic solvents not containing easily cleavable hydrogen atoms (e.g., hydroxy functional solvents). Useful inert diluents not containing easily cleavable hydrogen atoms include preferably aliphatic, alicyclic or aromatic (and optionally halogenated) hydrocarbons, such as, for example, benzine, ligroin, benzene, toluene, xylene, chlorobenzene, dichlorobenzene, hexane, heptane, octane, cyclohexane, methylcyclohexane; ethers, such as, for example, methyl t-butyl ether, diisopropyl ether, diisobutyl ether, dioxane, tetrahydrofuran or ethylene glycol dimethyl ether or ethylene glycol diethyl ether; and nitriles, such as acetonitrile, propionitrile or butyronitrile.

Aromatic hydrocarbons, such as, for example, toluene, xylene or chlorobenzene, are particularly preferred as diluents in the process according to the invention.

The presence of an inert diluent of the type noted is required during the first reaction since water formed during the reaction must be removed.

The reaction temperatures may be varied over a relatively wide range in the process according to the invention. Generally—as mentioned above—the first step is carried out at temperatures between 0° C. and 150° C., preferably between 80° C. and 130° C., and the second step is carried out between 20° C. and 120° C., preferably between 40° C. and 90° C.

The process according to the invention is generally carried out at atmospheric pressure. However, it is also possible to carry out the process according to the invention at elevated or reduced pressure—in general between 0.1 bar and 10 bar.

To carry out the process according to the invention, in the first step generally 0.9 to 2.0 mol, preferably 1.0 to 1.2 mol, of hydrazine hydrate and 1 to 50 mmol, preferably 2 to 30 mmol, of catalyst and, in the second step, 1 to 5 mol, preferably 1.1 to 2.5 mol of phosgene are employed per mole of carboxylic acid of the formula (II).

In a preferred embodiment of the process according to the invention, the carboxylic acid of the formula (II), together with the inert diluent, is initially charged and the hydrazine hydrate and the catalyst are metered in any order. The reaction mixture is then heated until the reaction (first step) has ended, and the water liberated is removed using a water separator. To carry out the second step, the mixture is optionally diluted with additional inert diluent and phosgene is passed through until the reaction has ended. The inert diluent is subsequently distilled off under reduced pressure and the crude product obtained as residue is optionally purified by vacuum distillation (cf. the preparation examples).

After the first step of the process according to the invention has been carried out, the carboxylic hydrazides of the formula (III) can, if desired, be readily isolated after hot filtration by cooling and filtration or filtration with suction in order to remove the catalyst.

The substituted oxadiazolones of the formula (I) to be prepared by the process according to the invention are already known as starting materials for herbicidally active compounds (cf. European patent 321,833).

PREPARATION EXAMPLES

Example 1

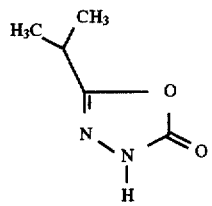

At room temperature (about 20° C.), 30 g (0.6 mol) of hydrazine hydrate are added dropwise with stirring to a solution of 44.1 g (0.5 mol) of isobutyric acid in 90 ml of toluene. At about 45° C., 1.42 g (5 mmol) of titanium tetra-i-propoxide are then added, and the reaction mixture is subsequently heated to the boil in a water separator for about two hours. During this time, about 23 ml of water are separated off. The titanium dioxide formed is separated off by boiling hot filtration (and can be reused as catalyst). The filtrate is diluted with 400 ml of toluene while still hot. At about 70° C. to 80° C., 55.5 g of phosgene are then passed through the solution over a period of about 2 hours. The solution is then allowed to cool and the solvent is distilled off under reduced pressure.

62.4 g (97.5% of theory) of 5-i-propyl-1,3,4-oxadiazol-2 (3H)-one are obtained as a liquid of slightly pink color.

Example 2

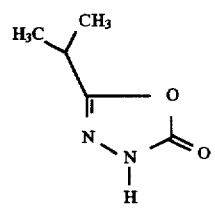

At room temperature (about 20° C.), 25 g (0.5 mol) of hydrazine hydrate are added dropwise with stirring to a mixture of 44 g (0.5 mol) of isobutyric acid, 1.4 g (5 mmol) of titanium tetra-i-propoxide and 90 ml of toluene. The mixture is heated to 100° C. for 3 hours, and while the mixture is still hot, the catalyst (recyclable) is separated off by filtration and the filtrate is subsequently diluted with 500 ml of toluene. At about 70° C. to 80° C., 55.5 g of phosgene are then passed through the mixture over a period of about 2 hours. The mixture is then allowed to cool slightly, the solvent is distilled off under reduced pressure and the product is purified by vacuum distillation.

56.3 g (88% of theory) of 5-i-propyl-1,3,4-oxadiazol-2 (3H)-one of boiling point 108° C. to 110° C. at 3–4 mbar are obtained.

Example 3

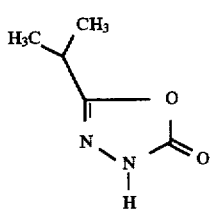

At room temperature (about 20° C.), 30 g (0.6 mol) of hydrazine hydrate are added dropwise with stirring to a solution of 44.1 g (0.5 mol) of isobutyric acid in 90 ml of toluene. At about 45° C., 10 g of aluminum oxide (acidic) are then added and the reaction mixture is subsequently heated to the boil for about two hours using a water separator. About 23 ml of water are separated off. To remove the catalyst (recyclable), the mixture is filtered while still hot and the filtrate is diluted with 400 ml of toluene. At about 70° C. to 80° C., 55.5 g of phosgene are then passed through the solution over a period of about 2 hours. The solution is then allowed to cool slightly and filtered, and the solvent is distilled off from the filtrate under reduced pressure.

61.2 g (95.6% of theory) of 5-i-propyl-1,3,4-oxadiazol-2 (3H)-one are obtained as a liquid of slightly pink color.

Preparation and isolation of the carboxylic hydrazides of the formula (III)

Example (III-1)

225 g (4.4 mol) of hydrazine hydrate are added to a mixture of 356 g (4.0 mol) of isobutyric acid and 1 liter of toluene. After the addition of 35.5 g (0.12 mol) of titanium tetra-i-propoxide, the mixture is heated to the boil using a distillation column and a water separator. 164 g of an "aqueous phase" (consisting of water, isopropanol and hydrazine) are separated off within a period of about 5 hours. The catalyst (recyclable) is then separated off from the hot mixture by filtration. Using the methods of Examples 1 to 3, the filtrate can be reacted further in a second step. To determine the yield, the solvent is distilled off under reduced pressure.

397 g of isobutyric hydrazide (purity: 98.8%, yield: 96% of theory) are obtained as a solid colorless residue.

Example (III-2)

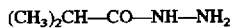

225 g (4.4 mol) of hydrazine hydrate are added to a mixture of 356 g (4.0 mol) of isobutyric acid and 1 liter of toluene. After the addition of 21.1 g (0.12 mol) of titanium catalyst (prepared separately in advance by reacting titanium tetra-n-propoxide with water), the mixture is heated to the boil using a distillation column and a water separator. After about one hour, the catalyst (recyclable) is filtered off while the mixture is still boiling hot (20.4 g, 97% recovery) and washed with hot toluene. Using the methods of Examples 1 to 3, the filtrate can be reacted further in a second step. To determine the yield, the filtrate is cooled to about 10° C. and the resulting crystalline product is isolated by filtration with suction.

408 g of isobutyric hydrazide (purity: 98.4%, yield: 98% of theory) are obtained.

Example (III-3)

214.5 g (4.2 mol) of hydrazine hydrate are added to a mixture of 356 g (4.0 mol) of isobutyric acid and 1 liter of toluene. After the addition of 12.8 g (0.16 mol) of titanium dioxide, the mixture is heated to the boil using a distillation column and a water separator. After about 90 minutes, (separation of 116 g of "aqueous phase"), the catalyst (recyclable) is separated off from the hot solution by filtration (12.4 g, 97% recovery) and washed with hot toluene. Using the methods of Examples 1 to 3, the filtrate can be reacted further in a second step. To determine the yield, the solvent is distilled off under reduced pressure.

410 g of isobutyric hydrazide (purity: 97.9%, yield: 98% of theory) are obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a carboxylic hydrazide of the formula R—CO—NH—NH$_2$ comprising reacting a carboxylic acid of the general formula

with hydrazine hydrate in the presence of a catalyst and in the presence of an inert diluent at temperatures between 0° C. and 150° C. with elimination of water and removal of said catalyst and wherein R represents an alkyl group which may be substituted.

2. A process for preparing substituted oxadiazolones of the general formula (I)

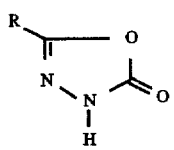

comprising a) reacting a carboxylic acid of the general formula (II)

with hydrazine hydrate in the presence of a catalyst and in the presence of an inert diluent at temperatures between 0° C. and 150° C. with elimination of water and removal of said catalyst and, b) reacting the resulting carboxylic hydrazide of the general formula (III)

in a second step with phosgene (COCl$_2$) at temperatures between 200° C. and 120° C., wherein in each of the formulas noted, R represents an alkyl group which may be substituted.

3. The process of claim 2, wherein in the formulae (I), (II) and (III), the radical R represents a straight-chain or branched alkyl having 1 to 6 carbon atoms, which may be substituted with halogen-atoms or C$_1$–C$_4$-alkoxy groups.

4. The process of claim 2, wherein in the formulae (I), (II) and (III), the radical R represents an alkyl group selected from the group consisting of methyl, ethyl, n-propyl, i-propyl, n-butyl, i-butyl, s-butyl and t-butyl, each of which may be substituted with a moiety selected from the group consisting of fluorine, chlorine, methoxy and ethoxy.

5. The process of claim 2, wherein the first process step is carried out at temperatures between 80° C. and 130° C.

6. The process of claim 2, wherein the second process step is carried out at temperatures between 400° C. and 90° C.

7. The process of claim 2, wherein said catalyst is selected from the group consisting of aluminum oxide, titanium dioxide, zirconium oxide, aluminum alkoxide, titanium alkoxide, zirconium alkoxide, aluminum halide alkoxide, titanium halide alkoxide and zirconium halide alkoxide.

8. The process of claim 7, wherein said catalyst is selected from the group consisting of aluminum tri-i-propoxide, titanium tetramethoxide, titanium tetraethoxide, titanium tetra-n-propoxide, titanium tetra-i-propoxide, titanium tetra-n-butoxide, titanium tetra-i-butoxide and titanium tetra-s-butoxide.

9. The process of claim 7, wherein said catalyst is selected from the group consisting of aluminum oxide, titanium dioxide, titanium tetra-n-propoxide and titanium tetra-i-propoxide.

* * * * *